United States Patent [19]

Ross

[11] Patent Number: 5,352,240

[45] Date of Patent: Oct. 4, 1994

[54] HUMAN HEART VALVE REPLACEMENT WITH PORCINE PULMONARY VALVE

[75] Inventor: Donald N. Ross, London, England

[73] Assignee: Promedica International, Inc., Newport Beach, Calif.

[21] Appl. No.: 359,478

[22] Filed: May 31, 1989

[51] Int. Cl.⁵ .............................................. A61F 2/24
[52] U.S. Cl. .......................................... 623/2; 623/1; 600/36
[58] Field of Search .................... 623/1, 2, 3, 11, 66

[56] References Cited

U.S. PATENT DOCUMENTS

| | | | |
|---|---|---|---|
| 4,218,782 | 8/1980 | Rugg | 623/2 |
| 4,343,048 | 8/1982 | Ross et al. | 623/2 |
| 4,350,492 | 9/1982 | Wright et al. | 623/2 |
| 4,372,743 | 2/1983 | Lane | 623/2 |
| 4,443,895 | 4/1984 | Lane | 623/2 |
| 4,477,930 | 10/1984 | Totten et al. | 623/2 |
| 4,790,844 | 12/1988 | Ovil | 623/2 |

*Primary Examiner*—David Isabella
*Attorney, Agent, or Firm*—Lyon & Lyon

[57] ABSTRACT

A method of treating heart valve dysfunction in a human patient in which the dysfunctioning valve is replaced with a novel bioprosthesis. The novel bioprosthesis comprises a porcine pulmonary valve, which has preferably been treated to fix and also sterilize the valve tissue. The porcine pulmonary valve may either be stent mounted to facilitate its surgical implantation into the patient, or it may be unstented to reduce the possibility of embolism and thrombosis.

6 Claims, 1 Drawing Sheet

5,352,240

HUMAN HEART VALVE REPLACEMENT WITH PORCINE PULMONARY VALVE

FIELD OF THE INVENTION

This invention relates to the field of medicine, and in particular to a method of treating heart valve dysfunction in a human patient by replacing the existing valve with a porcine pulmonary valve.

TECHNOLOGY REVIEW

The human heart includes two valved chambers (left and right ventricles) for pumping blood through the body. Each ventricle has two valves to control flow of the blood into and out of it. In the case of the right ventricle they are the tricuspid and pulmonary valves and in the case of the left ventricle, the mitral and aortic valves. During each cycle of the heart's operation, the mitral and tricuspid valves are simultaneously opened to allow blood to flow into the ventricles while the aortic and pulmonary valves are closed. The ventricles then contract, and the resulting blood pressure therein closes the mitral and tricuspid valves while opening, and forcing blood outward through, the aortic and pulmonary valves. The aortic and pulmonary valves in humans are both trileaflet valves, being similar to one another in both size and anatomy. This is also true of the aortic and pulmonary valves of a pig. However, in both humans and pigs the pulmonary valve is a more delicate structure with a thinner arterial wall and more flexible, symmetric leaflets than the corresponding aortic valve since it functions on the right side of the heart under lower blood pressure.

In some individuals one or more valves may not function normally, usually as a result of disease-induced valve damage, degeneration or a congenital defect. In the case of the aortic valve, in particular, dysfunction often results from a narrowing of the valve orifice (stenosis), or from valve incompetence such that the valve does not fully open or close. Severe valve dysfunction is life threatening. For the past 25 years, severe valve dysfunction has been treated by replacing the valve with a mechanical prosthesis, or alternatively, with a tissue valve (i.e., a valve of human or animal tissue). Tissue valves have the advantage of a lower incidence of blood clotting (thrombosis). Hence patients receiving such a valve, unlike those receiving a mechanical valve, do not require prolonged anticoagulation therapy with the potential clinical complications, expense, and patient inconvenience. In the case of human aortic valve replacement, the most common tissue valves can be categorized as allografts (usually aortic valves from cadavers, sometimes referred to as homogafts) or xenografts (animal heart valves). In addition, some human aortic valves have been replaced with pulmonary autografts, that is a pulmonary valve from the same patient which in turn is then replaced with an allograft (homograft) or tissue valve constructed from non-valvular tissue (e.g. pericardium). The use of pulmonary autografts to replace a patient's aortic valve, is first described by Ross, *Lancet*, 1967, Vol. 2, 956; and also later described by Matsuki et al., *J. Thorac and Cardiovas. Surg.*, Vol. 95, p. 705 (1988); and "Tissue Heart Valves", ed. M. I. Ionescu, publisher Butterworth Inc., Boston, Mass., U.S.A. (1979) particularly at pp. 146–172. The foregoing references and all other references cited herein, are incorporated by reference.

Xenografts are commonly used for human valve replacement, particularly the porcine aortic valve since it is similar in anatomy to the human aortic valve (both being trileaflet, i.e. tricuspid) and is readily available in a variety of sizes. The porcine aortic xenograft has been used for human valve replacement, both stented (i.e. mounted in a frame such as those described in "Tissue Heart Valves", supra., particularly at pp. 32–34, 107–109, and 177), and unstented. Because unstented valves minimize turbulence they should reduce thrombosis and embolism. However, they require a more exacting surgical procedure for insertion into a patient than a stented valve and can only be used in the aortic position. It is also known that the porcine aortic valve should first be treated with an agent, typically glutaraldehyde, to fix the valve tissue, sterilize it, and decrease its antigenicity.

The porcine aortic valve, is not identical to the human aortic valve. An important distinction is that the porcine aortic valve, unlike the human aortic valve, has a muscle shelf which extends into one of the valve cusps (the right-coronary cusp). The muscle shelf prevents the right coronary cusp from completely opening, thereby partially obstructing blood flow. This obstruction is accentuated with smaller diameter valves. Thus, when a patient's valve is replaced with a porcine aortic valve of the same diameter, blood flow becomes more impeded. This problem is more severe in patient's with small diameter valves (e.g., children). Attempts have been made to compensate for this problem. For example, in aortic valve replacement, techniques have been advocated to enlarge a patient's aortic annulus (the portion of the heart in which the valve is seated) so that a porcine aortic valve having a diameter greater than that of the patient's aortic valve, could be used. Alternatively, valves have been produced by a technique in which the right coronary cusp of the porcine aortic valve has been replaced with a non-coronary cusp from another porcine aortic valve. However, such techniques require additional manipulations of the patient's aortic annulus or the porcine aortic valve, with their attendant difficulties and expense.

SUMMARY OF THE INVENTION

The present invention provides a method of treating valve dysfunction in a human patient, by replacing the existing valve with a novel bioprosthesis of the present invention which comprises a porcine pulmonary valve. Preferably, the porcine pulmonary valve has been treated either in the same manner that porcine aortic valves have previously been treated with glutaraldehyde or with some similar fixing and sterilizing agent prior to implantation into a patient. Such treatment fixes the valve tissue to produce increased valve strength and durability, while at the same time reduces antigenicity of the valve tissue and sterilizes the valve. The porcine pulmonary valve used for the foregoing method, can either be stent mounted in a manner analogous to that by which porcine aortic valves have previously been stent mounted, or it can be unstented.

The present invention therefore provides a bioprosthesis, comprising a porcine pulmonary valve, which, when unstented, is suitable for replacing the human aortic or pulmonary valves, or which, when stented, is suitable for replacing the human aortic, mitral or tricuspid valves. The method of replacing the human valve with the porcine pulmonary valve, offers all of the advantages of using the porcine aortic valve for such a purpose, but in addition eliminates a major disadvantage of using the latter valve, namely asymmetry of the cusps and the presence of the muscle shelf therein which results in restricted blood flow.

Previously, the porcine pulmonary valve has not been considered as a replacement for a human valve, since the porcine pulmonary valve was regarded as a more delicate structure, and hence perceived to be less durable than the porcine aortic valve. However, it follows that the treatment of the porcine pulmonary valve with fixing, sterilizing and preserving agents will result in a valve of sufficiently increased durability for replacing the human valve, without the attendant disadvantages of a porcine aortic valve replacement.

DRAWINGS

Embodiments of the invention will now be described with reference to the drawings, in which.

DETAILED DESCRIPTION OF THE EMBODIMENTS OF THE INVENTION

Figure 1:
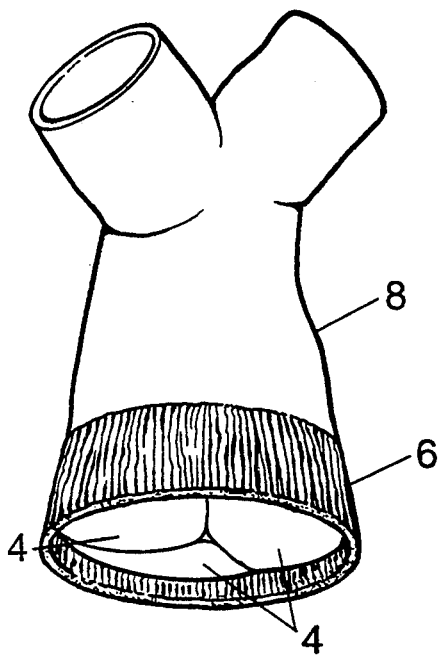
FIG. 1 is a perspective view of an unstented porcine pulmonary valve with an attached pulmonary aortic artery segment.

Referring first to FIG. 1, there is shown an excised porcine pulmonary valve 2 which essentially consists of three cusps or leaflets 4. Valve 2, in particular all three cusps 4 thereof, is attached to pulmonary annulus 6 and swings in the upward direction in FIG. 1 when blood is pumped out of the left ventricle. A segment 8 of the porcine pulmonary artery has been excised with valve 2. At this point the unitary combination of valve 2, pulmonary annulus 6 and segment 8, would be treated with a fixing agent, preferably glutaraldehyde, to fix the tissue. A bioprosthesis, which can be implanted to replace a human patient's valve, can then be prepared from valve 2 by one of two preferred methods as described below.

Figure 2:
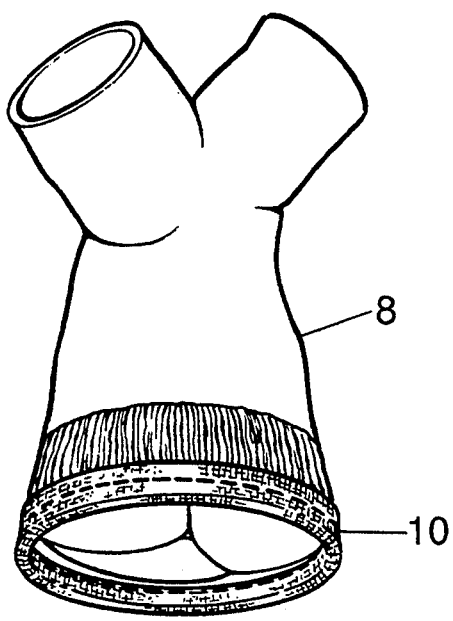
FIG. 2 is a perspective view similar to FIG. 1, except showing the presence of a sewing skirt which has been sutured adjacent the inflow side of the valve.

In the first method, a flexible sewing skirt 10, preferably made from synthetic polymer such as those sold under the trademarks DACRON or TEFLON, is simply sutured to pulmonary annulus 6 adjacent the inflow side of valve 2, as shown in FIG. 2. The resulting unstented porcine pulmonary valve can then be sterilized and stored in the same manner as known for unstented porcine aortic valves.

Figure 3:
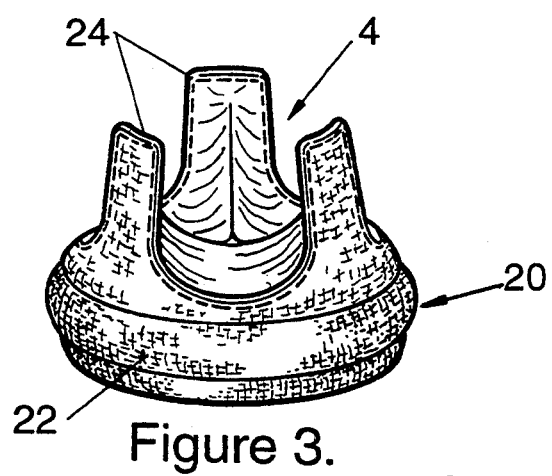
FIG. 3 is a perspective view of a stent-mounted porcine pulmonary valve.

In the alternative, second method, segment 8 of the porcine pulmonary artery, including the bifurcation, is removed and the remaining valve structure 2 is sutured to a conventional stent 20 as shown in FIG. 3. Stent 20 is preferably made of metal, and has three upstanding, symmetrical and inwardly flexible legs 24, as well as a sewing ring 22. Both the structure of stent 20 and the manner of suturing the porcine pulmonary valve 2 thereto, are analogous to the well known stents and suturing techniques used to prepare a stented porcine aortic valve. For example, see "Tissue Heart Valves", supra., particularly at pp. 32–34, 107–109 and 177. The resulting stented valve can then be sterilized and stored in the same manner, and under the same conditions, as the unstented valve of FIG. 2.

The resulting fixed and sterile porcine pulmonary valve 2, both stented (FIG. 3), and unstented with a sewing skirt (FIG. 2), can then be used to replace a human patient's valve using well known surgical techniques. For example, the unstented porcine pulmonary valve 2 with sewing skirt 10 (FIG. 2) can replace a human aortic valve using essentially the same surgical technique as in the replacement of the human aortic valve with an allograft (i.e., homograft). For example, see Ross, *J. Card. Surg.*, 2 (Supp.) 179 (1987), and "Tissue Heart Valves," supra., particularly pp. 146–149. In the case of the stented porcine pulmonary valve of FIG. 3, this can, for example, be used to replace a human aortic valve by essentially the same surgical technique as used to replace a human aortic valve with a stented porcine aortic valve. See, for example, "Tissue Heart Valves," supra., particularly at p. 122. However, it will be understood that the stented porcine pulmonary valve 2 of FIG. 3 is considered suitable only for replacing the human aortic, mitral, or tricuspid valves. The unstented porcine pulmonary valve 2 of FIG. 2, on the other hand, is considered suitable only for replacing the human aortic or pulmonary valves. Sewing skirt 10, in the case of the unstented valve 2 of FIG. 2, and sewing ring 22, in the case of the stent mounted valve 2 of FIG. 3, facilitate suturing of the valve to the patient's valve annulus.

In replacing the human aortic or pulmonary valves, it is preferred that the bioprosthesis of FIG. 2 (unstented porcine pulmonary valve with sewing skirt), be used, since it will likely result in lower turbulence and lower incidence of thrombosis. However, as is known, stented heart valves are surgically easier to implant than unstented valves. Thus, the bioprosthesis of FIG. 3 (the stented porcine pulmonary valve) may be preferred by some surgeons over the bioprosthesis of FIG. 2.

Figure 4:
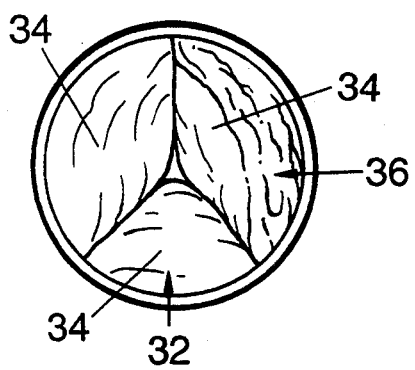
FIG. 4 is a view of a porcine aortic valve from the inflow side, and which shows this valve's muscle shelf.
Figure 5:
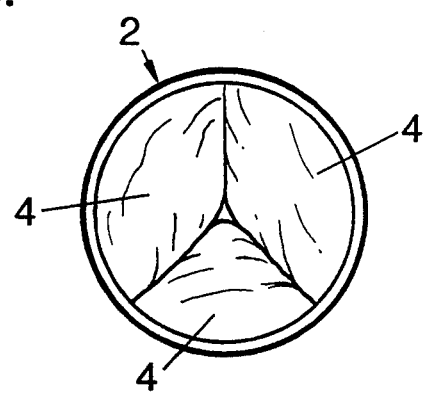
FIG. 5 is a view of a porcine pulmonary valve from the inflow side.

Whether the stented or unstented porcine pulmonary valve is used to replace a human heart valve, a greater blood flow through that bioprosthesis is obtained over a porcine aortic valve of the same diameter. The reason for this can be seen from a comparison of FIGS. 5 and 4, which respectively show a porcine pulmonary valve 2 used in the bioprosthesis of the present invention, and a porcine aortic valve 32, both viewed from the inflow side. The porcine aortic valve 32 has 3 cusps as does the porcine pulmonary valve 2. However, porcine aortic valve 32 has a muscle shelf 36 which extends onto one of cusps 3 (in particular, the right coronary cusp) preventing that cusp from opening to the same extent as the remainder of cusps 34. Porcine pulmonary valve 2, which is used in the bioprosthesis of the present invention, can therefore provide superior blood outflow rates with lower turbulence, than can conventional porcine aortic valves of the same diameter.

It will be appreciated that modifications to the embodiments described in detail above, are of course possible. Accordingly, the present invention is not limited to the embodiments which have been described in detail above.

I claim:

1. A method of treating aortic or pulmonary valve dysfunction in a human patient, comprising replacing the existing dysfunctioning valve with a fixed and sterilized whole excised unstented pulmonary porcine valve.

2. A method as in claim 1 wherein the porcine valve includes a section of porcine pulmonary artery associated with the porcine valve.

3. A method as in claim 1 wherein said porcine valve has attached thereto a flexible sewing skirt extending from the inlet side of the porcine valve to facilitate suturing of the valve in the patient.

4. A method of treating aortic or pulmonary valve dysfunction in a human patient comprising fixing and sterilizing an unstented pulmonary porcine valve, and replacing the existing dysfunctioning valve with the fixed and sterilized whole unstented pulmonary porcine valve.

5. A method of treating aortic or pulmonary valve dysfunction in a human patient comprising excising a whole porcine pulmonary valve and associated section of porcine pulmonary artery, fixing and sterilizing the pulmonary porcine valve and artery, and replacing the existing dysfunctioning valve with the fixed and sterilized whole pulmonary porcine valve which is unstented.

6. A method of treating aortic or pulmonary valve dysfunction in a human patient comprising excising a whole porcine pulmonary valve and associated section of porcine pulmonary artery, fixing and sterilizing the pulmonary porcine valve and artery, attacing a flexible sewing skirt to the porcine valve extending from the inlet side thereof to facilitate suturing of the valve in the patient, and replacing the existing dysfunctioning valve with the fixed and sterilized whole pulmonary porcine valve which is unstented.

* * * * *